United States Patent [19]
Sasaki et al.

[11] Patent Number: 5,916,924
[45] Date of Patent: Jun. 29, 1999

[54] REMEDIES FOR LIVER DISEASES

[75] Inventors: Hajime Sasaki; Atsushi Nemoto; Hisae Kume; Hiroshi Tsuboi; Kenji Mizumoto, all of Odawara; Naommy Takahashi, Tokyo; Masayuki Uchida, Odawara, all of Japan

[73] Assignee: Meiji Milk Products Co., Ltd., Tokyo, Japan

[21] Appl. No.: 08/971,267

[22] Filed: Nov. 17, 1997

[51] Int. Cl.$^6$ .................................................. A61K 31/13
[52] U.S. Cl. .......................................... 514/667; 514/669
[58] Field of Search ..................... 514/669, 667

[56] References Cited

FOREIGN PATENT DOCUMENTS 8-310944  11/1996  Japan .

OTHER PUBLICATIONS

Hajime Sasaki, et al, Proc. Natl. Acad. Sci. USA, vol. 94, pp. 7320–7325, "Ethanolamine Modulates the Rate of Rat Hepatocyte Proliferation in Vitro and in Vivo", Jul. 1997.
Hajime Sasaki, et al., In Vitro Cell Dev. Biol.–Animal, vol. 34, pp. 68–73, "Stimulation of Rat Hepatocyte Proliferation in Vitro and in Vivo by Factors Derived from the Bovine Small Intestinal Mucosa", Jan. 1998.

*Primary Examiner*—Jerome D. Goldberg
*Attorney, Agent, or Firm*—Oblon, Spivak, McClelland, Maier & Neustadt, P.C.

[57] ABSTRACT

The present invention discloses a method for the treatment of liver diseases, comprising administering an effective amount of an aminoalcohol of the following formula (1) or a salt thereof:

$$HN\!\!\begin{array}{c}(CH_2)_n-OR^1\\R^2\end{array} \quad (1)$$

wherein $R^1$ represents a hydrogen atom or a phosphono group, $R^2$ represents a hydrogen atom or a group—$(CH_2)_n$—$OR^1$, and n represents an integer between 2 and 5 inclusive. The present invention also relates to the use of the compound in the manufacture of a remedy for the treatment of liver diseases. This compound exhibits hepatocyte proliferation activity and liver disorder restoring effect, and thus is useful for the treatment of acute hepatitis, chronic hepatitis, hepatic cirrhosis, etc.

3 Claims, 4 Drawing Sheets

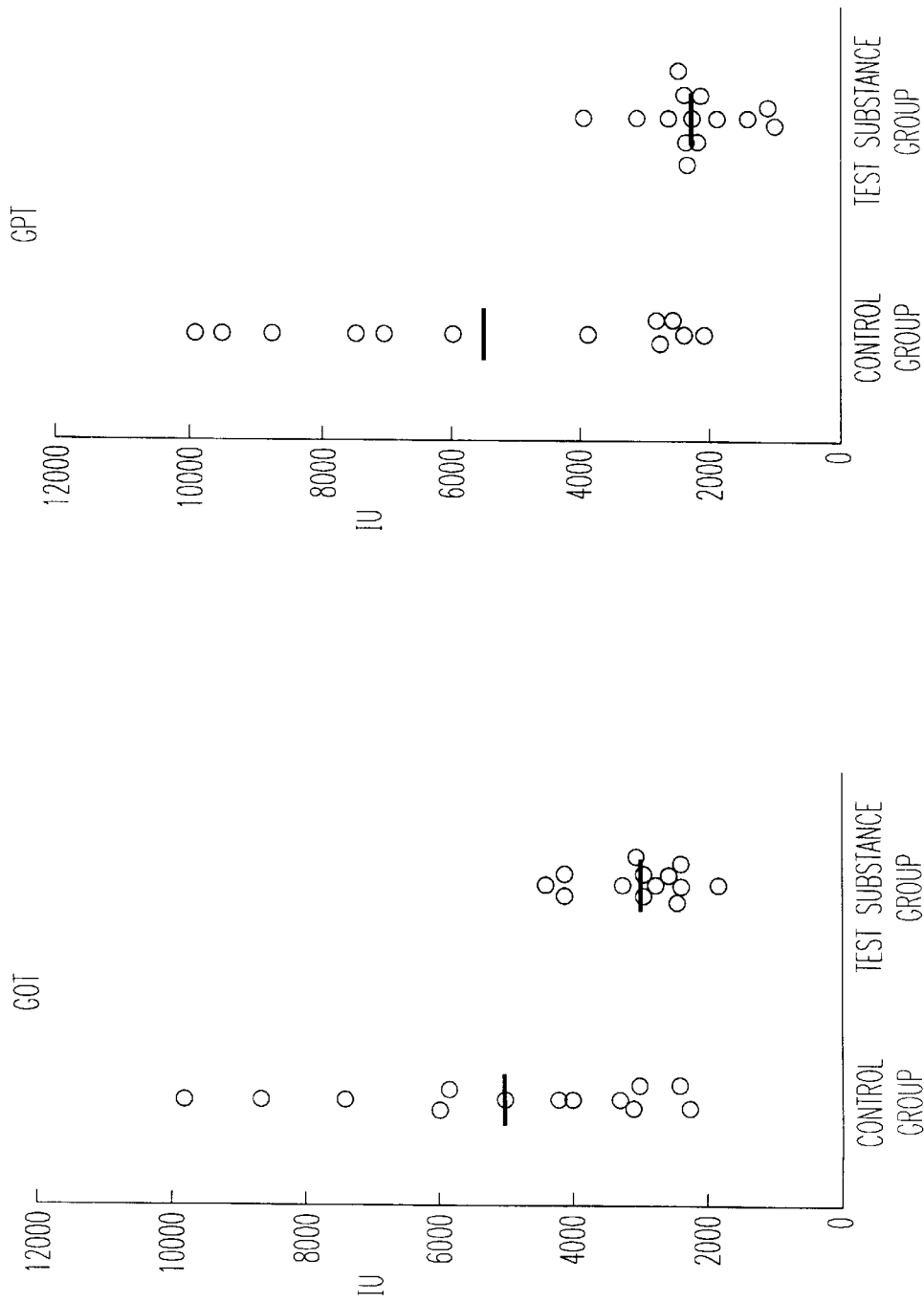

REMEDIES FOR LIVER DISEASES

BACKGROUND OF THE INVENTION

1. Technical Field

The present invention relates to remedies for liver diseases such as acute hepatitis, chronic hepatitis, liver cirrhosis, and liver cancer.

2. Background Art

The liver is an organ having a strong regenerative power. In rats, when 70% of the liver parenchyma is removed, the remaining mesenchymal tissue begins to proliferate. Although this phenomenon, liver regeneration, has been considered to be induced by the participation of a certain humoral factor, the mechanism has remained unknown.

In 1984, Nakamura et al. discovered a hepatocyte growth factor (HGF) in blood of a rat having a liver that was in the course of regeneration (Nakamura, T. et al., "Biochem. Biophys. Res. Commun.", 122: 1450–1459, 1984). This discovery was achieved by use, as an index, of the DNA synthesis of hepatocytes of a mature rat in primary culture. Thereafter, cloning of the HGF cDNA satisfactorily led to the determination of the entire primary structure (Nakamura, T. et al., "Nature," 342: 440–443, 1989). As a result, HGF was found to be a new growth factor that has homology with no previously known growth factor whose structure had conventionally been clarified, such as epithelial growth factor (EGF), fibroblast growth factor (FGF), neuronal growth factor (NGF), platelet-derived growth factor (PDGF), or endothelial cell growth factor (ECGF).

In the meantime, Takahashi et al. cultured rat hepatocytes for a long period by use of an extract of epithelial mucosa of the bovine small intestine, and found that hepatocytes proliferate, through orderly aggregation and rearrangement of cells, form liver tissue-like construct and come to newly exhibit some of the liver functions (Takahashi, N. et al.: "In vitro Cellular & Developmental Biology, 25:365–372, 1989). Although there have been attempts to isolate and purify the growth factor contained in this extract and also to determine the structure of the growth factor, no such attempts have been successful so far.

The aforementioned HGF discovered by Nakamura et al. has been found to act as a potent mitogen not only on hepatocytes but also on primary culture of tubular epithelial cells, dermal keratinocytes and melanocytes, type II epithelial cells of pulmonary alveolus, and epithelial cells of gastric mucosa. In addition, it has also been elucidated that HGF has a function as a motogen to stimulate motion of cells as well as action to suppress proliferation of cancer cells.

Research and development of pharmaceuticals making use of diversified biological activities of HGF have currently performed actively. For example, clinical applications of HGF have been explored towards remedy and prevention of hepatitis and renal disorders, promotion of regeneration of the liver after hepatectomy, treatment of wounds, and use as anticancer agents. However, no efforts have been successful in using HGF in practical medicine.

SUMMARY OF THE INVENTION

Accordingly, the object of the present invention is to find out a factor or an ingredient—other than the conventionally known HGF—that proliferates liver parenchymal cells, and to apply such a factor or ingredient to pharmaceutical products.

In view of the foregoing, the present inventors fractionated an extract of bovine small intestine epithelial mucosa tissue in various ways, using the hepatocyte growth promoting activity as an index, and found the following: a high molecular weight fraction exhibited in vitro hepatocyte proliferation activity by themselves, whereas a low molecular weight fraction did not exhibit strong in vitro hepatocyte proliferation activity by themselves; their activity was first exhibited in the presence of a high molecular weight fraction. However, during research of in vivo hepatocyte proliferation activities, the inventors found that a low molecular weight fraction exhibited excellent activities when administered alone. They continued the research, and found that the active substance of the low molecular weight fraction was in fact ethanolamine, that analogous activities are possessed by other alkanolamines, and that these alkanolamines exhibited excellent preventive and therapeutic effects against a variety of liver disease models, thus leading to completion of the invention.

In one aspect of the present invention, there is provided a method for the treatment of liver diseases, comprising administering an effective amount of an aminoalcohol of the following formula (1) or a salt thereof:

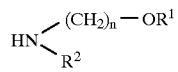

(1)

wherein $R^1$ represents a hydrogen atom or a phosphono group, $R^2$ represents a hydrogen atom or a group $-(CH_2)_n-OR^1$, and n represents an integer between 2 and 5 inclusive.

In another aspect of the present invention, there is provided use of the aminoalcohol of the above-described formula (1) or a salt thereof in the manufacture of a remedy for liver diseases.

The above and other objects, features, and advantages of the present invention will become apparent from the following description.

BRIEF DESCRIPTION OF THE DRAWINGS

FIG. 2 shows a decrease in GOT when ethanolamine was intraperitoneally administered to mice having a liver disorder induced by carbon tetrachloride.

FIG. 3 shows a decrease in GPT when ethanolamine was intraperitoneally administered to mice having a liver disorder induced by carbon tetrachloride.

PREFERRED EMBODIMENTS OF THE INVENTION

Figure 1:
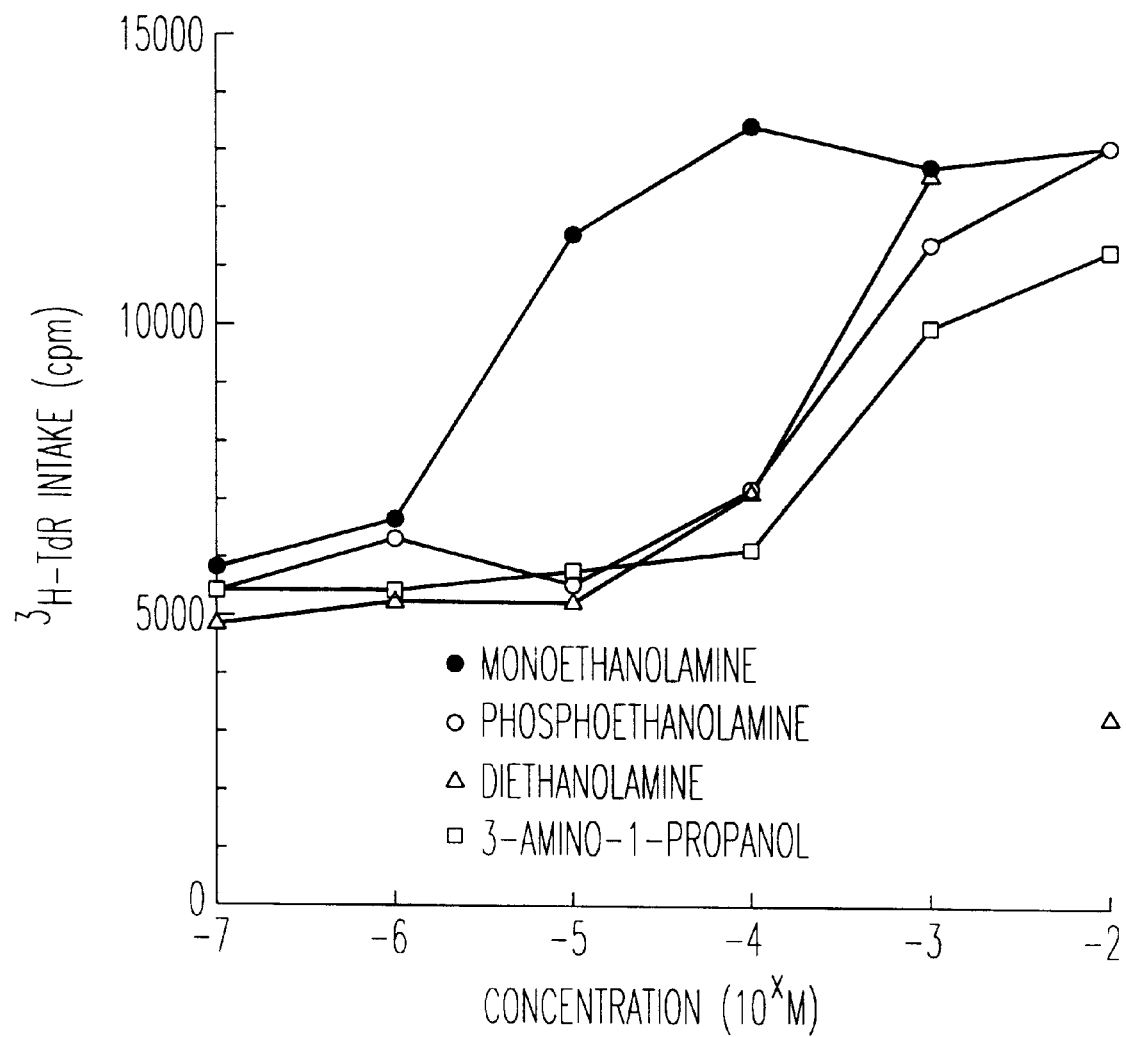
FIG. 1 is a graph showing the hepatocyte growth promoting activity of several aminoalcohols by way of $^3$H-TdR uptake (cpm).
Figure 4:
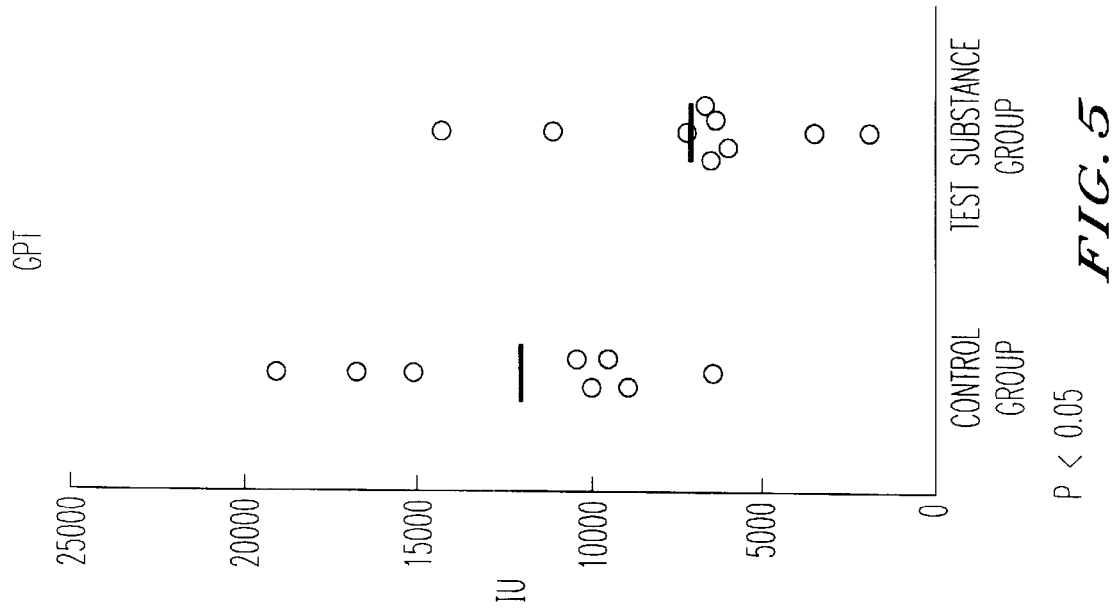
FIG. 4 shows a decrease in GOT when ethanolamine was perorally administered to mice having a liver disorder induced by carbon tetrachloride.
Figure 5:
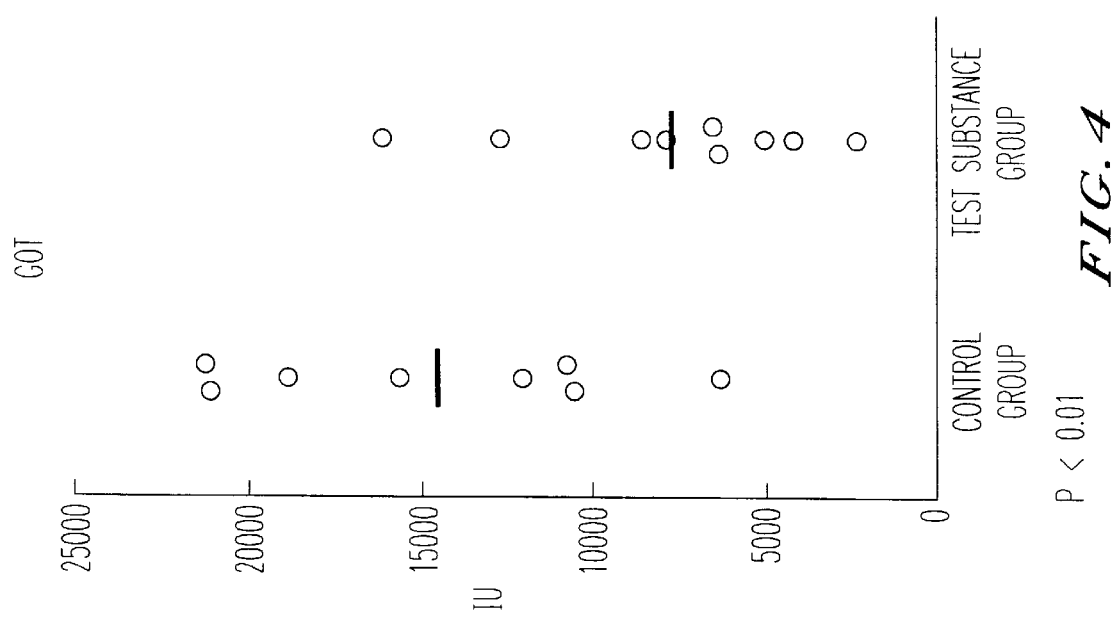
FIG. 5 shows a decrease in GPT when ethanolamine was perorally administered to mice having a liver disorder induced by carbon tetrachloride.

Examples of preferred aminoalcohols of formula (1) which may be used in the present invention include monoethanolamine, monopropanolamine, monobutanolamine, monopentanolamine, diethanolamine, dipropanolamine, phosphoethanolamine, and phosphopropanolamine. Of these, monoethanolamine, diethanolamine, phosphoethanolamine, and monopropanolamine are particularly preferred. In formula (1), n is preferably 2 or 3. Although no particular limitation is imposed on the salts of the aminoalcohol of formula (1) so long as they are pharmacologically acceptable, chlorides, sulfates, and other acid-addition salts are preferred.

In the present invention, a commercially available aminoalcohol may directly be used as the aminoalcohol of formula (1). Alternatively, it may be chemically synthesized by a method known per se. Also, regarding the ethanolamine, the aforementioned low molecular fraction obtained from an extract of epithelial mucosa of the bovine small intestine may directly be used.

In order to collect a low molecular fraction containing ethanolamine from an extract of epithelial mucosa of the bovine small intestine, epithelial mucosa of the bovine small intestine may be extracted with methanol, and components that precipitate at low temperature may be removed if necessary.

Aminoalcohols of formula (1) and salts thereof exhibit hepatocyte proliferation promoting activity and therapeutic effect in hepatitis models and hepatic cirrhosis models, and in addition, they are quite safe. Therefore, aminoalcohols of formula (1) and salts thereof are useful as therapeutic agents for acute hepatitis, chronic hepatitis, hepatocirrhosis, and liver cancer, and also as liver regeneration stimulators after hepatectomy.

Aminoalcohols of formula (1) and salts thereof may be administered by either perorally or parenteraly, and the remedies for liver diseases according to the present invention may have a variety of forms including peroral preparations such as powders, granules, tablets, sugar-coated tablets, capsules, and ampules; injection preparations such as subcutaneous, intramuscular, or intravascular injections; and suppositories.

The remedies of the present invention for liver diseases may be manufactured by sole use of an aminoalcohol of formula (1), or by use in suitable combination of an aminoalcohol of formula (1) and any of pharmacologically acceptable carriers such as vehicles, bulking agents, binders, humectants, disintegrants, surfactants, lubricants, dispersants, buffers, preservatives, flavors, perfumes, coating agents, etc.

The dose of the thus-prepared remedies of the present invention for liver diseases differs in accordance with the condition of the disease, administration route, etc. However, in general, the dose (as reduced to the amount of aminoalcohol of formula (1)) for an adult is 10–5,000 mg/day, preferably 50–2,000 mg/day, which is preferably administered at a time or in 3–4 divided times.

EXAMPLES

The present invention will next be described in more detail by way of examples, which should not be construed as limiting the invention thereto.

Example 1
Method of Preparation of High Molecular Weight Factor and Low Molecular Weight Factor Crude Extracts Epithelial mucosa was excised with a razor blade from the muscle fascicle of water-rinsed bovine small intestine and stored at $-80°$ C.

The frozen tissue was thawed at room temperature by use of methanol (2 liters per 500 g of tissue) and homogenized in a blender. The homogenate was kept at $4°$ C. for about 8 h and filtered through a filter paper in a Buchner funnel, to thereby obtain an extract. To the residue on the funnel, methanol (1 liter) was added and the mixture was allowed to stand overnight. Another extract from the mixture obtained in the similar manner was combined with the previous one. The combined extract was concentrated through evaporation of methanol. To the concentrated extract (about 50 ml), the same amount of methanol was added and the resultant precipitate was removed by centrifugation (3000 rpm, 10 min). Further, after evaporation of methanol from the supernatant, the extract was combined with pure water to make the total volume 50 ml and stored at $4°$ C. The precipitate produced during the storage was removed and low molecular weight factor crude extract was obtained. This extract was used as a starting material for purification of the low molecular weight factor.

The residue (100 g) retained after extraction of low molecular weight factor was combined with phosphate buffered saline (500 ml; 10 mM sodium phosphate, pH 7.4, 150 mM NaCl), and the mixture was subjected to extraction with stirring overnight at $4°$ C. The supernatant collected by centrifugation (10,000 rpm, 30 min) at $4°$ C. was used as high molecular weight factor extract. The extract was stored in aliquots at $-20°$ C.

Example 2
Separation and Identification of Factors Showing Hepatocyte Proliferation Promoting Activity In separation and identification of the low molecular weight factor showing hepatocyte proliferation promoting activity derived from epithelial mucosa of the bovine small intestine, the rat hepatocyte system in primary culture was used. To this culture system, a fraction of a crude extract of bovine small intestine epithelial mucosa in the course of purification was added in the presence of high molecular weight factor extract (1%) and insulin (10 $\mu$g/ml) or in the presence of EGF (20 ng/ml) and insulin (10 $\mu$g/ml), to thereby establish an assay system for measuring the uptake of $^3$H-TdR into DNA of rat hepatocyte nuclei.

The crude extract from the bovine small intestine epithelial mucosa (10 ml) was fractionated by use of a Sephacryl S-100 column (5×28 cm, Pharmacia). Fractions each amounting 15 ml was added to the above-mentioned assay system and the uptake of $^3$H-TdR was measured. The above column was equilibrated with pure water at a flow rate of 3 ml/min. Detection was based on ultraviolet absorption (280 nm).

The fractions with activity resulting from the gel filtration by use of Sephacryl S-100 gel were pooled and concentrated to 10–20 times the original concentration in a rotary evaporator at $60°$ C. The concentrate (2 ml) was subjected to a Capcel Pac C18 reverse phase column (2×25 cm, 5 $\mu$m particular diameter, Shiseido). Elution was performed by an isocratic method, in which 20 mM Tris-HCl (pH 7.4) solution containing 3% acetonitrile was used as a buffer. The flow rate was 4 ml/min and the detection was based on ultraviolet absorption (220 nm).

However, since satisfactory results of separation were not obtained, phenylisothiocyanate (PITC)—which is a hydrophobic group—was bound to the amino group contained in each fraction, to thereby create a PTC derivative which easily adsorbs on the reverse phase HPLC column. The fractions with activity (1 ml) were combined with ethanol (7 ml), triethylamine (1 ml) and PITC (1 ml), reacted for 30 min at room temperature, and dried in a centrifugal vaporizer. The dried material was dissolved in methanol (0.5 ml) and diluted with pure water (1.5 ml).

The diluted solution was filtered through a filter membrane (0.45 $\mu$m) and subjected to a C18 reverse phase column (2×25 cm, Hibar C18, RT250-20, Cica-Merck, Kanto Chemical K.K.). The filtrate was loaded in a 40° C. column. The components adsorbed on the column were eluted by an eluent obtained by mixing Solution A (acetonitrile 3%, sodium acetate 17 mM (pH 5.4)) and Solution B (acetonitrile 90%, sodium acetate 17 mM (pH 5.4)) so as to have a concentration gradient of acetonitrile.

The component existing only in the fractions exhibiting activity was detected as a PTC derivative when the activity was measured prior to creation of the PTC derivative. The molecular weight of the component was measured by LC-MASS, and it was found that the molecular weight before binding with PITC was 61. Further, the component which had transformed into a PTC derivative was collected and its structure was analyzed by NMR. As a result, the component was found to have a chemical structure represented by $NH_2CH_2CH_2OH$.

Since this substance was monoethanolamine, a monoethanolamine sold on the market was added to the above-mentioned rat hepatocyte system in primary culture, and the $^3H$-TdR uptake activity was measured. As a result, they showed a synergistic growth-stimulating effects similar to the effect exhibited by the low molecular weight active component in the presence of either the high molecular weight factor extract or EGF (FIG. 1). FIG. 1 also shows the effects by other alkanolamines. The activity in the extract of small intestine epithelial mucosa was clearly attributed to monoethalonamine.

Example 3
Liver Regeneration Experiments

Male Sprague-Dawley rats (6–8 weeks old, 200–250 g) were used in all experiments. Rats were fed ordinary food and water. 70% hepatectomy was conducted by excising the rectangular lobe, the median lobe, and the left lateral lobe.

Liver regeneration experiments were conducted according to the following methods. There were used physiological saline solution (1 ml/rat) as a negative control, glycyrrhizin (SNMC) (2 mg/rat) as a control, 100 mM monoethanolamine-HCl (EA-HCl) (1 ml/rat) as a test sample (prepared by adjusting the pH of a Wako specialty grade monoehanolamine (Wako Pure Chemicals) to 6.84 with hydrochloric acid and diluting with physiological saline solution), and a crude extract of bovine small intestine epithelial mucosa (1 ml/rat).

After twenty two hours following the administration, 2.5 ml of a mixture of BrdU (5-bromodeoxyuridine, 10 mg/ml, Sigma) and 5-fluoro-2'-deoxyuridine (1 mg/ml, Sigma) was intraperitoneally injected to each rat. Two hours later, the liver was excised and fixed in 100% methanol overnight. After dehydration with ethanol, samples were dealcoholated with xylene, and embedded in paraffin at 58° C. Paraffin sections (4 μm thick) were made and fixed on preparations, and subjected to the below-described immunohistochemistry.

After removal of paraffin from samples by a conventional method, the samples were treated with 0.3% $H_2O_2$ (in methanol) for 30 minutes at room temperature and washed twice (each time for 3 minutes) with $H_2O$ so as to block endogenous peroxidase. Subsequently, the samples were treated with 2N HCl for 30 minutes at room temperature, neutralized with 0.1N $Na_2B_4O_7$ for 3 minutes, and washed three times with PBS (each time for three minutes). The subsequent reactions were conducted by use of a detection kit (Cell Proliferation Kit; Amersham RPN 20) (GRATZNER, H. G. et al, Exp. Cell. Res., 95, pp. 88–94, 1975., GRATZNER, H. G., Science, 218, pp. 474–475, 1982). First, the samples were reacted with anti-BrdU mouse IgG for 1 hour at room temperature, then were washed three times with PBS (each time for three minutes). Next, they were reacted with peroxidase anti-mouse IgG2a for 30 minutes at room temperature, and washed three times with PBS (each time for three minutes). Lastly, the samples were reacted with DAB (3,3'-diamionobenzidine; 500 mg/1 liter) in phosphate buffer for 5 minutes at room temperature, washed twice with distilled water (each time for 5 minutes), and sealed after dehydration.

The nuclei of the cells in which BrdU were incorporated stained brown to black. For processing of the data, a photographs were taken, and a total of not less than 4,000 cells in the photo were counted to obtain the labeling index (%) expressed by {"the number of nuclei in which BrdU had been incorporated"/"the total number of cells"}×100. Immunohistochemistry was simultaneously performed on both the candate lobe and the right lateral lobe. Almost the same results were obtained. The results obtained from the candate lobe are shown in Tables 1 and 2.

Also, the corresponding labeling indices obtained in the case in which monoethanolamine was administered to a group of healthy rats are shown in Table 3 for reference.

TABLE 1

Stimulation of liver regeneration after partial hepatectomy (stimulated by use of a crude extract of bovine small intestine epithelial mucosa and monoethanolamine)

| Slice No. | Substance administered | BrdU labeling index (%) | Mean ± SD |
|---|---|---|---|
| 219 | Physiol. saline | 33.4 (1911/5723) | 33.2 ± 5.9 (n = 7) |
| 329 | Physiol. saline | 31.8 (1326/4175) | |
| 331 | Physiol. saline | 39.9 (2083/5219) | |
| 348 | Physiol. saline | 21.8 (1126/5172) | |
| 349 | Physiol. saline | 37.1 (1921/5172) | |
| 350 | Physiol. saline | 37.1 (1917/5172) | |
| 351 | Physiol. satine | 31.1 (1608/5172) | |
| 296 | Crude extract 1 ml/rat | 51.9 (936/1803) | 50.0 ± 4.9 (n = 6)*** |
| 320 | Crude extract 1 ml/rat | 49.0 (2805/5723) | |
| 336 | Crude extract 1 ml/rat | 45.4 (2370/5219) | |
| 355 | Crude extract 1 ml/rat | 54.7 (2827/5172) | |
| 356 | Crude extract 1 ml/rat | 55.4 (2951/5172) | |
| 358 | Crude extract 1 ml/rat | 43.5 (2032/5172) | |
| 313 | EA-HC1 10 mg/rat | 47.4 (2712/5723) | 43.9 ± 5.1 (n = 7)** |
| 332 | EA-HC1 10 mg/rat | 38.5 (2009/5219) | |
| 333 | EA-HC1 10 mg/rat | 51.8 (2706/5219) | |
| 334 | EA-HC1 10 mg/rat | 45.2 (2360/5219) | |
| 352 | EA-HC1 10 mg/rat | 45.1 (2331/5172) | |
| 353 | EA-HC1 10 mg/rat | 37.5 (1938/5172) | |
| 359 | EA-HC1 10 mg/rat | 41.6 (2150/5172) | |

Results are from respective rats that had undergone 70% hepatectomy
***: $P < 0.001$,
**: $P < 0.01$ (Student's t-test)

TABLE 2

Labeling indices when SNMC was administered to rats that had undergone partial hepatectomy

| Slice No. | Substance administered | BrdU labeling index (%) | Mean ± SD |
|---|---|---|---|
| 375 | Physiol. saline | 37.3 (1103/2960) | 33.5 ± 5.4 (n = 3) |
| 376 | Physiol. saline | 35.9 (1064/2960) | |
| 377 | Physiol. saline | 27.3 (809/2960) | |
| 374 | SNMC 2 mg/rat | 38.0 (1124/2960) | 33.1 ± 7.8 (n = 3) |
| 378 | SNMC 2 mg/rat | 37.3 (1104/2960) | |
| 379 | SNMC 2 mg/rat | 24.1 (476/1973) | |

Results are from respective rats that had undergone 70% hepatectomy

The amount of SNMC administered was expressed in terms of th amount of glycyrrhizin

TABLE 3

Labeling indices when monoethanolamine was administered to healthy rats

| Slice No. | Substance administered | BrdU labeling index (%) | Mean ± SD |
|---|---|---|---|
| 362 | Physiol. saline | 1.0 (64/6206) | 1.2 ± 0.3 (n = 3) |
| 363 | Physiol. saline | 1.2 (72/6206) | |
| 364 | Physiol. saline | 1.5 (92/6206) | |
| 365 | Crude extract 1 ml/rat | 1.2 (76/6206) | 1.0 ± 0.2 (n = 3) |
| 366 | Crude extract 1 ml/rat | 0.9 (58/6206) | |
| 357 | Crude extract 1 ml/rat | 1.0 (63/6206) | |
| 368 | EA-HC1 10 mg/rat | 1.0 (61/6206) | 1.2 ± 0.3 (n = 3) |
| 369 | EA-HC1 10 mg/rat | 1.1 (70/6206) | |
| 370 | EA-HC1 10 mg/rat | 1.5 (90/6206) | |

Example 4

GOT and GPT tests

Groups of mice in which liver disorder was induced by carbon tetrachloride were provided, and the restoring effect of ethanolamine (hepatocyte proliferation factor) on the liver disorder was investigated by use of reduction in serum transaminase (GOT or GPT) as an index.

(1) Animals ddY-Male mice (5 weeks old) were purchased and kept for three days to check the health conditions before being used in the test.

(2) Grouping

Each of the mice purchased was weighed, and classified in accordance with the body weight. The animals were grouped so that the groups, each consisting of 10 mice, represented almost the same average body weight. The grouping of mice was performed on the first day of administration, prior to administration of the test compounds.

(3) Preparation of carbon tetrachloride and ethanolamine

Carbon tetrachloride

Carbon tetrachloride (5 ml, Wako Pure Chemicals) was put in a glass vial, and Panasate 800 (45 ml, Nippon Yushi Chemicals Co, Ltd.) was added to prepare a 10% (v/v) solution.

Ethanolamine

Intraperitoneal administration: Ethanolamine (42 $\mu$l) was dissolved in physiological saline, and the pH was adjusted to 7 with HCl. Subsequently, the total amount was made to 50 ml. An aliquot of 2 ml was diluted in 38 ml of physiological saline.

(4) Manner of administration and dose

One group consisted of 10 mice. For 24 hours prior to the administration of tetrachloride, each mouse was fasted by being fed water only. 10% carbon tetrachloride/Panasate solution was intraperitoneally administered to each mice at a dose of 1 ml/kg. Twenty four hours after the administration of carbon tetrachloride, the test substance (i.e., ethanolamine) and the control (i.e., physiological saline) were administered. In the case of intraperitoneal administration, the substance (or saline) was re-administered 12 hours after the administration of the first administration of ethanolamine, and 6 hours after the re-administration, blood as collected. In the case of peroral administration, ethanolamine was administered only once, and blood was collected 24 hours thereafter.

In the test of intraperitoneal administration of ethanolamine, a group representing the dose equivalent to 2.8 mg/kg ethanolamine was compared with a control group, whereas in the test of peroral administration of ethanolamine, a group representing the dose equivalent to 16 mg/kg ethanolamine was compared with a control group. Details of groups provided for the tests of intraperitoneal administration and peroral administration are shown in Tables 4 and 5, respectively.

TABLE 4

| Group | Number of animals | Drug administered | Dose (mg/kg) | Concentration (mg/ml) | Soln. administered (ml/kg) | Administration (Times) |
|---|---|---|---|---|---|---|
| Control group | 10 | Physiol. saline | 0 | — | 10 | 2 |
| Test substance group | 10 | Ethanolamine | 2.8 | 0.28 | 10 | 2 |

TABLE 5

| Group | Number of animals | Drug administered | Dose (mg/kg) | Concentration (mg/ml) | Soln. administered (ml/kg) | Administration (Times) |
|---|---|---|---|---|---|---|
| Control group | 10 | Physiol. saline | 0 | — | 10 | 1 |
| Test substance group | 10 | Ethanolamine | 16 | 20 | 10 | 1 |

The animals were anesthetized with diethylether (Wako Pure Chemicals) and their abdominal potions were cut-open. Blood was collected from the abdominal aorta by use of 1-ml disposable syringes (Terumo). The blood, dispensed into 1.5 ml Eppendorf tubes, was subjected to centrifugal separation at 5,000 rpm for 10 minutes to thereby obtain serum. The activity of transaminase (GOT, GPT) in the serum thus obtained was measured. The measurement was performed by use of a Cobas Mira System (Baxter).

(5) Results

The results are shown in FIGS. 2 through 5. As is apparent from these drawings, it was confirmed that in both groups of intraperitoneal administration of ethanolamine (2.8 mg/kg) and peroral administration of ethanolamine (16 mg/kg), both GOT and GPT levels significantly decreased. In addition, there was noted a tendency that the area of necrosis was reduced in the histopathological profile of the liver.

Example 5
Effect on hegatic cirrhosis (1)

Groups of rats having hepatocirrhosis induced by N-nitrosodiethylamine were provided, and the effect of ethanolamine (hepatocyte proliferation factor) on the therapy of hepatocirrhosis was investigated by use of the histopathological finding as an index.

(1) Animals

Fifty Sprague-Dawley male rats (5 weeks old; Nippon SLC) were purchased and prebred for five days to check the health conditions before being used in the test.

(2) Grouping

Each of the rats purchased was weighed, and classified in accordance with the body weight. Thirty animals were selected and grouped into three groups so that the groups, each consisting of 10 rats, represented almost the same average body weight. The grouping of rats was performed on the first day of administration, prior to administration of the test compounds.

(3) Preparation of N-nitrosodiethylamine and ethanolamine

N-nitrosodiethylamine

An N-nitrosodiethylamine solution (5.32 ml; which corresponds to 5 g due to the specific gravity of 0.94) was measured into a measuring cylinder by use of a glass pipette, and physiological saline was added to make the total volume 100 ml. Subsequently, the solution was sonicated for 2 minutes (Sine Sonic 150, model UA 150; product of Shinmeidai Kogyo) to prepare a uniform N-nitrosodiethylamine solution (50 mg/ml).

Ethanolamine

Ethanolamine (3.05 ml) was dissolved in physiological saline and neutralized with HCl. The volume of the solution was adjusted to 50 ml by use of physiological saline. The resultant ethanolamine solution (10 ml) was diluted with physiological saline (36 ml).

(4) Manner of administration and dose

One group consisted of 10 rats. 100 mg/2 ml/kg of N-nitrosodiethylamine was intraperitoneally administered to each rat once in the morning on days 0, 7, 14, 21, and 28 (day 0: the first day of administration of N-nitrosodiethylamine). Ethanolamine was orally administered to each rat once in the afternoon everyday. As a control, physiological saline was administered instead of ethanolamine.

In the test of intraperitoneal administration of ethanolamine, a group representing the dose equivalent to 40 mg/kg ethanolamine base was compared with a control group. Details of groups provided for the test of intraperitoneal administration and control groups are shown in Table 6.

The rats were fasted overnight on the 6th day following the final administration of N-nitrosodiethylamine, and dissected on the following day; They were anesthetized with diethylether (Wako Pure Chemicals) and the liver was removed. The liver, after being visually observed and then weighed, was fixed with 10% neutral formalin buffer, and allowed to stand for more than 24 hours. Subsequently, the liver sample was embedded in paraffin by a conventional method, so as to prepare sliced sections. The sections were subjected to hematoxylin-eosin staining and Masson trichrome staining and histopathologically observed for indications of hepatic cirrhosis. The indice of hepatic cirrhosis employed were nodule formation for visual observation, and formation of clear cell foci for histopathological inspection, in which the changes were classified into 4 levels. The number of individuals assigned to each level was counted.

(6) Results

Histopathological inspection revealed that clear cell foci were found in all cases of all groups. The results are shown in Table 7, in which the levels of changes are classified into 4 grades of light (+1), medium (+2), severe (+3), and very severe (+4). In Table 7, numerical figures denote the number of corresponding cases in each group containing ten rats.

TABLE 7

| Group | Levels | | | |
| --- | --- | --- | --- | --- |
|  | +1 | +2 | +3 | +4 |
| Control group | 0 | 5 | 4 | 1 |
| Test substance group | 6 | 2 | 2 | 0 |

The clear cell foci were hepatocyte hyperplastic foci and pressurized the surrounding parenchyma. They had clear periphery, and were not directly correlated to the pseudo lobe or nodules. They corresponded to the foci of cellular alteration in accordance with the nomenclature recommended by the NTP (The National Toxicology Program). In all the cases of the control group, the clear cell foci were determined as "medium" to "very severe," whereas in the test substance group, 6 cases were determined as "light." According to the Dunnett's statistical test, there was a significant difference between the control group and the test substance group with respect to the extent of formation of clear cell foci (level of significance: $P<0.05$).

Example 6
Effect on hepatic cirrhosis (2)

(Method)

Groups Sprague-Dawley male rats (7 weeks old; Nippon SLC) were purchased and kept for five days before being used in the test. Each group consisted of 10 rats, and four groups were used in the test. The first group represented non-treatment (i.e., control group), the second group represented use of N-nitrosodiethylamine alone, the third group represented N-nitrosodiethylamine plus 15 mg/kg

TABLE 6

| Group | Number of animals | Drug administered | Dose (mg/kg) | Concentration (mg/ml) | Soln. administered (ml/kg) | Administration (Times) |
| --- | --- | --- | --- | --- | --- | --- |
| Control group | 10 | Physiol. saline | 0 | — | 3 | Twice a week |
| Test substance group | 10 | Ethanolamine | 40 | 13.3 | 3 | Twice a week | ethanolamine, and the fourth group represented N-nitrosodiethylamine plus 50 mg/kg ethanolamine.

An N-nitrosodiethylamine solution (5.32 ml; which corresponds to 5 g due to the specific gravity of 0.94) was measured into a measuring cylinder by use of a glass pipette, and physiological saline was added to make the total volume 100 ml. Subsequently, the solution was sonicated for 2 minutes to prepare a uniform N-nitrosodiethylamine solution (50 mg/ml). The solution was prepared just before use. N-nitrosodiethylamine was intraperitoneally administered to each rat at a dose of 100 mg/2 ml/kg once in the morning on days 0, 7, 14, 21, and 28 (day 0: the first day of administration of N-nitrosodiethylamine).

An ethanolamine hydrochloric acid salt was measured and dissolved in a certain amount of distilled water for injection use. The solution was suitably diluted and administered to each rat by oral route by use of an oral probe for rats. The details are summarized in Table 8.

TABLE 8

| Dose (Ethanolamine base equivalent) (mg/kg) | Concentration of soln. (Ethanolamine. HCl equivalent) (mg/ml) | Soln. administered (mg/kg) | Administration (times) |
| --- | --- | --- | --- |
| 0 | — | 10 | every day |
| 15 | 2.4 | 10 | every day |
| 50 | 50 | 10 | every day |

The animals were fasted overnight on the 6th day (day 34) following the final administration of N-nitrosodiethylamine, and dissected on the following day (day 35); They were anesthetized with diethylether (Wako Pure Chemicals), blood was collected from the dorsal aorta, and the liver was removed. The liver was visually observed, and then a portion thereof was fixed with 10% neutral formalin buffer. Portions of fixed samples were frozen and stored at −80° C. in a tightly-sealed container.

The liver tissue fixed with neutral formalin buffer was embedded in paraffin by a customary method, so as to prepare sliced sections. The sections were subjected to hematoxylin·eosin staining or Masson trichrome staining for histopathological observation.

The frozen liver tissue (1 g) was weighed and homogenized in a Teflon homogenizer together with pure water (3 ml). The homogenate (1 ml) was mixed with an equal amount of concentrated HCl, and the mixture was sealed in glass ampule while air was purged under a nitrogen stream. After sealing, the contents were hydrolyzed for 24 hours at 110° C. Subsequently, a portion of the hydrolyzate was subjected to an amino acid analysis. The amino acid analysis was performed through a phenylthiocarbamoil method (Heinrikson, R. L. and Meredith, S. S. (1984) "Analytical Biochemistry" 136, 65–74). As an index of fibrosis, the amount of hydroxyproline was used, and the hydroxyproline content per g of liver tissue was calculated for comparison.

(Results)

Figures 6, 7:
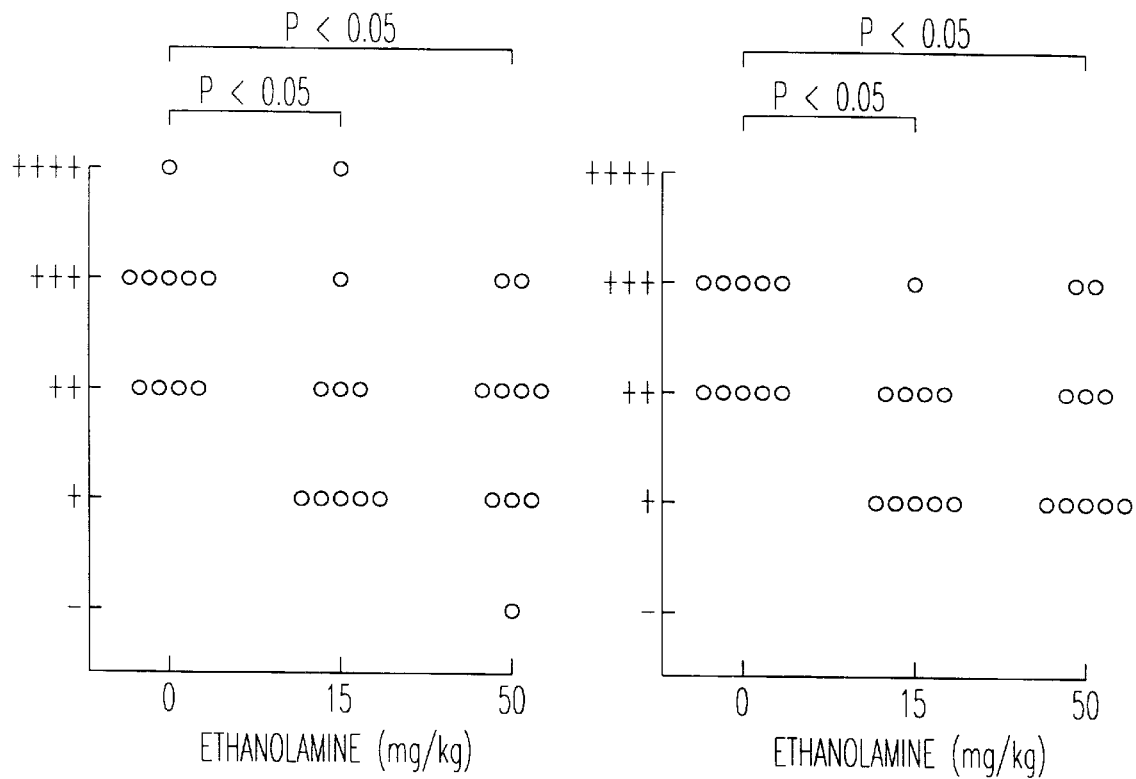
FIG. 6 shows effect of ethanolamine on nodule formation on the liver surface in rats having hepatic cirrhosis induced by the administration of N-nitrosodiethylamine.
FIG. 7 shows effect of ethanolamine on the formation of clear cell hyperplastic foci in rats having hepatic cirrhosis induced by the administration of N-nitrosodiethylamine.

(1) When the excised liver was visually observed, the N-nitrosodiethylamine administration group presented clear nodules in the surface of the liver, whereas in the ethanolamine administration group, the higher the dose of ethanolamine, the less significant the formation of nodules (FIG. 6). The formation of nodules was evaluated by five rankings. The results were studied for the significant difference by use of the Dunnet's test. The difference between each of the two ethanolamine administration groups (15 mg/kg and 50 mg/kg) and the N-nitrosodiethylamine group was statistically significant.

(2) The histopathological sections presented a considerable formation of clear cell foci in the N-nitrosodiethylamine administration group. In the ethanolamine administration groups, however, the higher the dose of ethanolamine, the less significant the formation of clear cell foci (FIG. 7). The formation of clear cell foci was evaluated by five rankings. The results were studied for the significant difference by use of the Dunnet's test. The difference between each of the two ethanolamine administration groups (15 mg/kg and 50 mg/kg) and the N-nitrosodiethylamine group was concluded to be statistically significant.

Figure 8:
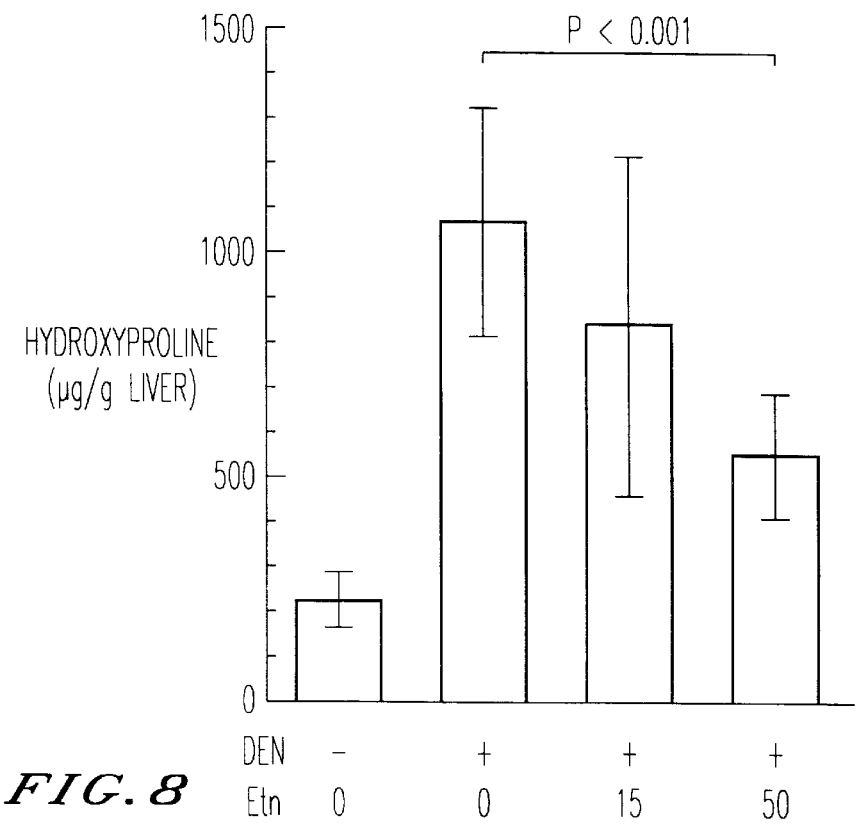
FIG. 8 shows effect of ethanolamine on the amount of hydroxyproline in rats having hepatocirrhosis induced by the administration of N-nitrosodiethylamine (NEN: N-nitrosodiethylamine, Etn: ethanolamine).

(3) The amount of hydroxyproline, serving as an index of fibrosis of the liver, was determined by an amino acid analysis. In the N-nitrosodiethylamine administration group, the hydroxyproline level significantly elevated, whereas in the ethanolamine administration groups, however, the higher the dose of ethanolamine, the lower the amount of hydroxyproline (FIG. 8). The results were studied for the significant difference by use of the t-test. The difference between the 50 mg/kg ethanolamine administration group and the N-nitrosodiethylamine group was concluded to be statistically significant.

The above results show that hepatic cirrhosis induced by N-nitrosodiethylamine can be prevented by oral administration of ethanolamine. It is considered that N-nitrosodiethylamine induces necrosis of hepatocytes and that in the necrotic area formed thereby, collagenous fiber proliferates to thereby form a pseudo lobe (Makoto Enomoto, 1991, "Liver" in "Toxicity Tests—5, Toxicity Pathology," Akihiko Maekawa and Yuzo Hayashi, Chijin Shokan, pp. 136–165). Thus, the nodules visually observed on the liver surface may result from the abnormal proliferation of hepatocytes induced by N-nitrosodiethylamine in the pseudolobule. In addition, the clear cell foci observed in the pathological sections may be equivalent to the nodules visually observed on the liver surface. Such nodules are formed when proliferation of hepatocytes comes to be active in the pseudolobule formed as fibrosis of the liver progresses. The abnormal proliferation of hepatocytes in the pseudolobule is considered to be caused by carcinogenic transformation of hepatocytes due to the carcinogenic action of hepatocytes (Scherer, E. and Emmelot, P. (1975), European Journal of Cancer 11, 689–696). That is, ethanolamine is considered to be effective in the prevention of a series of events including fibrosis of the liver, formation of a pseudolobule induced by fibrosis of the liver, and abnormal proliferation of hepatocytes in the pseudolobule, which progress in this order.

Example 7

Acute Toxicity Test

Monoethanolamine·HCl was dissolved in physiological saline at a concentration of 0.6 g/ml. The pH was adjusted to 7.0 by use of 5N NaOH. Solutions having lower concentrations were prepared by dilution with physiological saline. Each solution (10 μl) was intraperitoneally injected to mice (ICR, female, 6-weeks old, 29 g), and the survival ratio was obtained. Mice to which the solution was administered at doses of 5.0 and 2.5 g/kg died within 30 minutes of administration, whereas mice which received doses equal to or less than 1.25 g/kg were alive when six days had passed. The results are shown in Table 9.

TABLE 9

| Dose (Calculated as EA) (g/kg) | Administration (day) | Survival 1 day after admin. | 6 days after admin. |
|---|---|---|---|
| 5.0 | 0/4 | — | — |
| 2.5 | 0/4 | — | — |
| 1.25 | 3/3 | 3/3 | 3/3 |
| 0.5 | 4/4 | 4/4 | 4/4 |

As described above, the aminoalcohols of formula (1) and salts thereof according to the present invention—which exhibit hepatocyte proliferation activity—synergistically stimulate proliferation of hepatocytes in the presence of high molecular weight fraction of an extract of the small intestine epithelial mucosa of mammals or in the presence of EGF. Moreover, since the aminoalcohols of formula (1) and salts thereof of the present invention are low-molecular weight compounds and are biological components, they pose no problem such as antigenicity, toxicity, etc. When administered to living bodies, aminoalcohols of formula (1) or salts thereof per se stimulate division of hepatocytes and exhibit a liver disorder restoring effect. Therefore, the compounds are effective for the treatment of acute hepatitis, chronic hepatitis, hepatic cirrhosis, and liver cancer, as well as promotion of liver regeneration.

What is claimed is:

1. A method for the treatmentacute hepatitis, chronic hepatitis, hepatic cirrhosis or liver cancer, which is sensitive to a compound of formula (1), comprising: adminstering to a mammal in need thereof an effective amount of an aminoalcohol of the following formula(1) or a salt thereof:

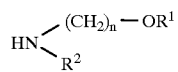

(1)

wherein $R^1$ represents a hydrogen atom, $R^2$ represents a hydrogen atom or a group —$(CH_2)_n$—$OR^1$, and n represents an integer between 2 and 5 inclusive.

2. The method according to claim 1, wherein n in formula (1) is 2 or 3.

3. The method according to claim 1, wherein the aminoalcohol of formula (1) is selected from the group consisting of monoethanolamine, diethanolamine, and monopropanolamine.

* * * * *

UNITED STATES PATENT AND TRADEMARK OFFICE
CERTIFICATE OF CORRECTION

PATENT NO. : 5,916,924

DATED : JUNE 29, 1999

INVENTOR(S): HAJIME SASAKI ET AL

It is certified that an error appears in the above-identified patent and that said Letters Patent is hereby corrected as shown below:

Column 14, line 4, "treatmentacute" should read --treatment of acute--.

Signed and Sealed this

Tenth Day of October, 2000

Q. TODD DICKINSON

*Attest:*

*Attesting Officer*     *Director of Patents and Trademarks*